United States Patent [19]

Petersen et al.

[11] Patent Number: 4,588,726
[45] Date of Patent: May 13, 1986

[54] 1-CYCLOPROPYL-6-FLUORO-1,4-DIHYDRO-4-OXO-7-(3-OXO-1-PIPERAZINYL)-3-QUINOLINECARBOXYLIC ACID ANTIBACTERIAL AGENTS

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 735,499

[22] Filed: May 17, 1985

[30] Foreign Application Priority Data

Jun. 4, 1984 [DE] Fed. Rep. of Germany ....... 3420770

[51] Int. Cl.[4] .................. A61K 31/495; C07D 401/02
[52] U.S. Cl. .................... 514/254; 544/363; 546/141
[58] Field of Search .................... 544/363; 514/254

[56] References Cited

U.S. PATENT DOCUMENTS 4,398,029  8/1983  Irikura et al. ................ 544/363
4,448,962  5/1984  Irikura et al. ................ 544/363
4,544,658 10/1985  Petersen et al. ............. 544/363

FOREIGN PATENT DOCUMENTS 0049355  4/1982  European Pat. Off. .
3306771  8/1984  Fed. Rep. of Germany ...... 544/363
2437406  4/1980  France .

*Primary Examiner*—Glennon H. Hollrah
*Assistant Examiner*—J. H. Turnipseed
*Attorney, Agent, or Firm*—Sprung Horn Kramer & Woods

[57] ABSTRACT

Novel antibacterially active 1-cyclopropyl-6-fluoro-1,4-dihydro-4-oxo-7-(3-oxo-1-piperazinyl)-3-quinolinecarboxylic acids of the formula

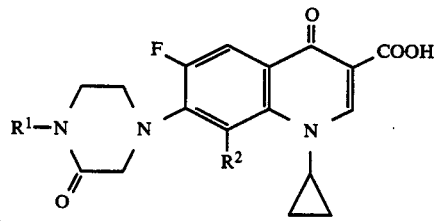

in which
$R^1$ is hydrogen, methyl or ethyl, and
$R^2$ is hydrogen or fluorine, and pharmaceutically tolerable hydrates and salts thereof.

10 Claims, No Drawings

1-CYCLOPROPYL-6-FLUORO-1,4-DIHYDRO-4-OXO-7-(3-OXO-1-PIPERAZINYL)-3-QUINOLINECARBOXYLIC ACID ANTIBACTERIAL AGENTS

The present invention relates to new 1-cyclopropyl-6-fluoro-1,4-dihydro-4-oxo-7-(3-oxo-1-piperazinyl)-3-quinolinecarboxylic acids, to process for their preparation and to antibacterial agents and feed additives containing them.

It has been found that the new 1-cyclopropyl-6-fluoro-1,4-dihydro-4-oxo-7-(3-oxo-1-piperazinyl)-3-quinolinecarboxylic acids of the formula (I)

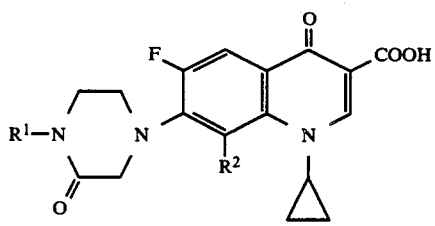

(I)

in which
R$^1$ denotes hydrogen, methyl or ethyl, and
R$^2$ denotes hydrogen or fluorine,
and their pharmaceutically utilizable hydrates, alkali metal and alkaline earth metal salts have high antibacterial activity.

It has also been found that the compounds of the formula (I) according to the invention are obtained when a compound of the formula (II)

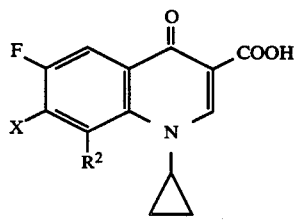

(II)

in which
R$^2$ has the abovementioned meaning, and
X represents chlorine, bromine or fluorine,
is reacted with a 2-piperazinone of the formula (III)

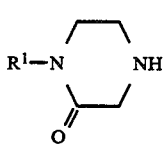

(III)

in which
R$^1$ has the abovementioned meaning.

Surprisingly, the 1-cyclopropyl-6-fluoro-1,4-dihydro-4-oxo-7-(3-oxo-1-piperazinyl)-3-quinolinecarboxylic acids according to the invention have a higher antibacterial activity than 1-ethyl-6-fluoro-1,4-dihydro-4-oxo-7-(1-piperazinyl)-3-quinolinecarboxylic acid which is known from the state of the art.

Thus, they are suitable as active compounds for human and veterinary medicine, veterinary medicine including also the treatment of fish for the therapy and prophylaxis of bacterial infections.

Thus, the substances according to the invention represent an enrichment of pharmacy.

When, for example, 1-cyclopropyl-6,7-difluoro-1,4-dihydro-4-oxo-3-quinolinecarboxylic acid and 2-piperazinone are used as starting substances, then the course of the reaction can be represented by the equation below:

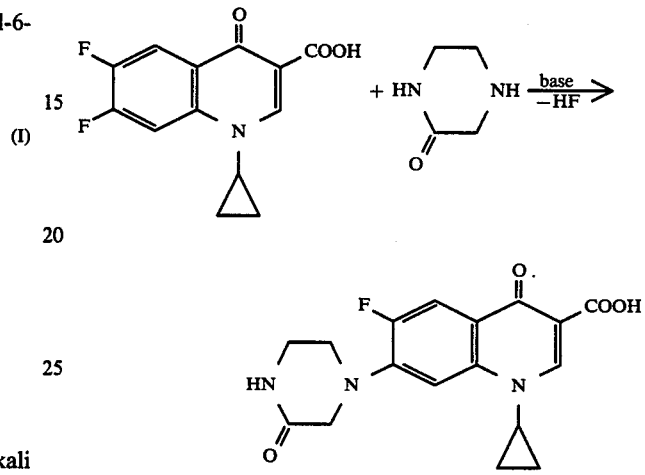

Some of the quinolonecarboxylic acids of the formula (II) which are used as starting compounds are known (application Ser. No. 614,923, filed May 29, 1984, now pending, corresponding to German Published Specification DOS No. 3,142,854: 7-chloro-1-cyclopropyl-6-fluoro-1,4-dihydro-4-oxo-3-quinolinecarboxylic acid) or they can be prepared by the following route:

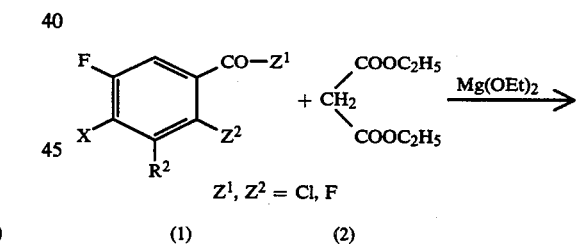

Z$^1$, Z$^2$ = Cl, F (1)    (2)

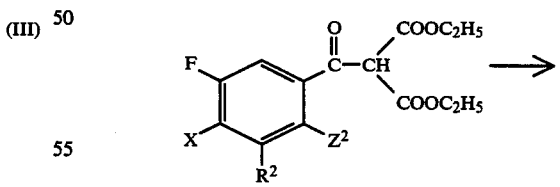

(3)

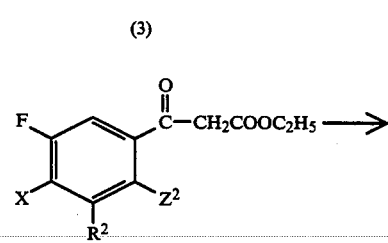

(4)

-continued

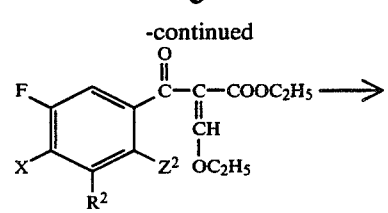
(5)

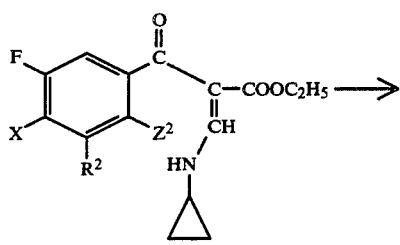
(6)

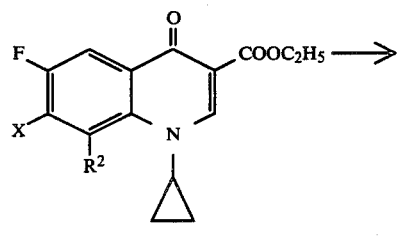
(7)

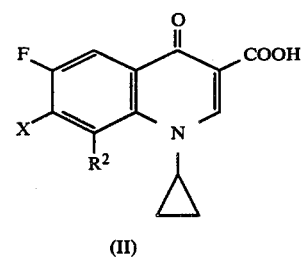
(II)

According to this, diethyl malonate (2) is acylated with the appropriate benzoyl flouride or chloride (1) in the presence of magnesium methylate to give the aroylmalonic ester (3) (Organicum, 3rd edition, 1964, page 438).

By partial hydrolysis and decarboxylation of (3) in aqueous medium using catalytic amounts of sulphuric acid or p-toluenesulphonic acid, the ethyl aroylacetate (4) is obtained in good yield, and this is converted with triethyl orthoformate/acetic anhydride into the corresponding ethyl 2-benzoyl-3-ethoxyacrylate (5). Reaction of (5) with cyclopropylamine in a solvent such as, for example, methylene chloride, alcohol, chloroform, cyclohexane or toluene leads, in a slightly exothermic reaction, to the desired intermediate (6).

The cyclization reaction (6)→(7) is carried out in a temperature range of about 60° to 300° C., preferably 80° to 180° C.

The diluents which can be used are dioxane, dimethyl sulphoxide, N-methylpyrrolidone, sulpholane, hexamethylphosphoric triamide and, preferably, N,N-dimethylformamide.

Suitable acid-binding agents for this reaction step are potassium tert.-butanolate, butyllithium, lithiumphenyl, phenyl magnesium bromide, sodium methylate, sodium hydride and sodium or potassium carbonate. When hydrogen fluoride is to be eliminated ($Z^2 = F$), potassium or sodium fluoride has also proved to be particularly suitable. It may be advantageous to use an excess of 10 mol-% of base.

The ester hydrolysis of (7) under basic or acidic conditions which is carried out in the last step leads to 1-cyclopropyl-6-fluoro-7-halogeno-1,4-dihydro-4-oxo-3-quinolinecarboxylic acid (II).

The 2,3,4,5-tetrafluorobenzoyl chloride (1) ($R^2 = X = Z^2 = F$, $Z^1 = Cl$) which is used as starting material for this synthetic route was obtained from 2,3,4,5-tetrafluorobenzoic acid which is known from the literature (G. G. Yakobson, V. N. Odinokov and N. N. Vorozhtsov Jr., Zh. Obsh. Khim. 36, 139 (1966)) with thionyl chloride in the customary manner. It has a boiling point of 75°–80° C./17 mbar. The 2,3,4,5-tetrafluorobenzoyl fluoride has a boiling point of 46 to 47° C./20 mbar $n_D^{20}$: 1.4375)

The 2,4,5-trifluorobenzoyl fluoride (1) ($R^2 = H$, $X = Z^1 = Z^2 = F$) which is used as starting material was prepared analogously from the 2,3,5-trifluorobenzoic acid which is known from the literature (I. J. DeGraw, M. Corey and W. A. Steiner, J. Chem. Eng. Data 13, 587 (1968)). It has a boiling point of 53°–56° C./18 mbar ($n_D^{20} = 1.4546$).

The piperazinones (III) which are used as starting materials are known from the literature (S. R. Aspinall, J. Amer. Chem. Soc. 62, 1202 (1940)).

The reaction of (II) with (III) is preferably carried out in a diluent such as dimethyl sulphoxide, N,N-dimethylformamide, hexamethylphosphoric trisamide, sulpholane, water, an alcohol, such as methanol, ethanol, n-propanol, isopropanol or glycol monomethyl ether, or pyridine. Likewise, mixtures of these diluents can be used.

All customary inorganic and organic acid-binding agents can be used as the acid-binding agent. These preferably include the alkali metal hydroxides, alkali metal carbonates, organic amines and amidines. The following may be specifically mentioned as particularly suitable: triethylamine, 1,4-diazabicyclo[2.2.2]octane (DABCO), excess amine (III) or 1,8-diazabicyclo[5.4.0]-undec-7-ene (DBU).

The reaction temperatures can be varied within a relatively wide range. In general, the process is carried out between about 20° and 200° C., preferably between 80° and 180° C.

The reaction can be carried out under atmospheric pressure as well as under elevated pressure. In general, it is carried out under pressures between about 1 and about 100 bar, preferably between 1 and 10 bar.

When carrying out the process according to the invention, 1 to 3 moles, preferably 1 to 1.5 moles, of the piperazinone (III) are used for 1 mole of the carboxylic acid (II).

Apart from the compounds listed as examples, the following may be specifically mentioned as new active compounds:

1-cyclopropyl-6-fluoro-1,4-dihydro-7-(4-methyl-3-oxo-1-piperazinyl)-4-oxo-3-quinolinecarboxylic acid 1-cyclopropyl-7-(4-ethyl-3-oxo-1-piperazinyl)-6-fluoro-1,4-dihydro-4-oxo-3-quinolinecarboxylic acid 1-cyclopropyl-6,8-difluoro-1,4-dihydro-7-(4-methyl-3-oxo-1-piperazinyl)-4-oxo-3-quinolinecarboxylic acid 1-cyclopropyl-6,8-difluoro-1,4-dihydro-7-(4-methyl-3-oxo-1-piperazinyl)-4-oxo-3-quinolineoarboxylic acid and 1-cyclopropyl-7-(4-ethyl-3-oxo-1-piperazinyl)-6,8-difluoro-1,4-dihydro-4-oxo-3-quinolinecarboxylic acid.

PREPARATION EXAMPLES

Preparation of the starting materials II

EXAMPLE A

1-Cyclopropyl-6,7,8-trifluoro-1,4-dihydro-4-oxo-3-quinolinecarboxylic acid

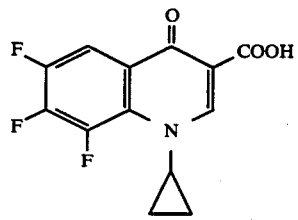

24.3 g of magnesium turnings are suspended in 50 ml of anhydrous ethanol. 5 ml of carbon tetrachloride are added and, when the reaction has started, a mixture of 160 g of diethyl malonate, 100 ml of absolute ethanol and 400 ml of anhydrous toluene is added dropwise at 50°-60° C. The mixture is then heated at 50°-60° C. for 1 hour, cooled to 5° C. to −10° C. with dry ice/acetone and, at this temperature, a solution of 212.5 g of 2,3,4,5-tetrafluorobenzoyl chloride in 80 ml of absolute toluene is slowly added dropwise. The mixture is stirred at 0° to −5° C. for 1 hour, allowed to reach room temperature overnight, and, while cooling in ice, a mixture of 400 ml of ice-water and 25 ml of concentrated sulphuric acid is allowed to run in. The phases are separated and two further extractions with toluene are carried out. The combined toluene solutions are washed with saturated NaCl solution, dried with $Na_2SO_4$, and the solvent is removed in vacuo. 335 g of diethyl 2,3,4,5-tetrafluorobenzoylmalonate are obtained as a crude product.

0.3 g of p-toluenesulphonic acid is added to an emulsion of 284.8 g of crude diethyl 2,3,4,5-tetrafluorobenzoylmalonate in 300 ml of water. The emulsion is heated to boiling for 5 hours, stirring vigorously, then it is cooled and extracted several times with methylene chloride, and the combined methylene chloride solutions are washed once with saturated NaCl solution, dried with $Na_2SO_4$, and the solvent is removed by distillation in vacuo. Fractionation of the residue under fine vacuum provides 160.2 g of ethyl 2,3,4,5-tetrafluorobenzoylacetate of boiling point 100°-110° C./0.09-0.1 mbar. Melting point 47°-49° C.

A mixture of 110.7 g of ethyl 2,3,4,5-tetrafluorobenzoylacetate, 93.5 g of ethyl orthoformate and 107 g of acetic anhydride is heated at 150° C. for 2 hours. The volatile constituents are then removed by distillation under waterpump vacuum and finally under high vacuum at a bath temperature of 120° C. 123.9 g of crude ethyl 2-(2,3,4,5-tetrafluorobenzoyl)-3-ethoxyacrylate remain behind. This is sufficiently pure for the further reactions.

23.2 g of cyclopropylamine are added dropwise to a solution of 123.9 g of ethyl 2-(2,3,4,5-tetrafluorobenzoyl)-3-ethoxyacrylate in 250 ml of ethanol, cooling in ice and stirring. When the exothermic reaction has subsided, the mixture is stirred at room temperature for 1 hour, the solvent is removed in vacuo, and the residue is recrystallized from cyclohexane/petroleum ether. 115 g of ethyl 2-(2,3,4,5-tetrafluorobenzoyl)-3-cyclopropylaminoacrylate of melting point 63°-65° C. are obtained.

21.2 g of sodium fluoride are added to a solution of 107.8 g of ethyl 2-(2,3,4,5-tetrafluorobenzoyl)-3-cyclopropylaminoacrylate in 400 ml of anhydrous dimethylformamide. The reaction mixture is then stirred under reflux for 2 hours and, while hot, poured onto ice. The precipitate is filtered off with suction, thoroughly washed with water and dried over calcium chloride at 100° C. in vacuo. 91.2 g of ethyl 1-cyclopropyl-6,7,8-trifluoro-1,4-dihydro-4-oxo-3-quinolinecarboxylate of melting point 167°-168° C. are obtained.

A mixture of 94 g of ethyl 1-cyclopropyl-6,7,8-trifluoro-1,4-dihydro-4-oxo-3-quinolinecarboxylate, 600 ml of glacial acetic acid, 450 ml of water and 70 ml of concentrated sulphuric acid is heated to reflux for 1.5 hours. The hot suspension is then poured onto ice, and the precipitate is filtered off with suction, thoroughly washed with water, and dried in vacuo at 100° C. In this manner, 88.9 g of pure 1-cyclopropyl-6,7,8-trifluoro-1,4-dihydro-4-oxo-3-quinolinecarboxylic acid of melting point 228°-230° C. (decomposition) are obtained.

EXAMPLE B

1-Cyclopropyl-6,7-difluoro-1,4-dihydro-4-oxo-3-quinolinecarboxylic acid

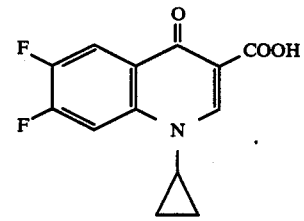

Starting from 2,4,5-trifluorobenzoyl fluoride, the process is carried out in analogy to Example A, the following steps being passed through: Diethyl 2,4,5-trifluorobenzoylacetate (boiling point=92°-95°/0.5 mbar; melting point: 53°-55° C.)→ethyl 2-(2,4,5-trifluorobenzoyl)-3-cyclopropylaminoacrylate (oil)→ethyl 1-cyclopropyl-6,7-difluoro-1,4-dihydro-4-oxo-3-quinolinecarboxylate (melting point: 230°-233° C.)→1-cyclopropyl-6,7-difluoro-1,4-dihydro-4-oxo-3-quinolinecarboxylic acid (melting point: 302°-303° C. with decomposition).

EXAMPLE 1

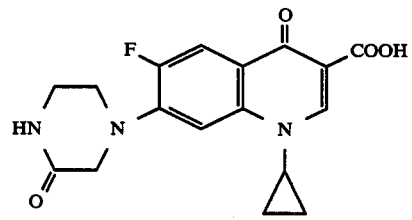

5.3 g (20 mmol) of 1-cyclopropyl-6,7-difluoro-1,4-dihydro-4-oxo-3-quinolinecarboxylic acid are initially introduced into 50 ml of DMSO and heated with 2.4 g (24 mmol) of 2-piperazinone and 4.4 g (40 mmol) of 1,4-diazabicyclo[2.2.2]octane at 130° C. for 1 hour. After cooling, the suspension is adjusted to pH 5 with 2 N hydrochloric acid, 50 ml of water are added, and the precipitate is filtered off with suction, washed with water and methanol, and then boiled in 50 ml of methanol. 5 g (72% of theory) of 1-cyclopropyl-6-fluoro-1,4-dihydro-4-oxo-7-(3-oxo-1-piperazinyl)-3-quinolinecarboxylic acid of melting point 342°–348° C. (decomposition) and purity 97% (HPLC) are isolated. Mass spectrum: m/e 345 (M+), 301 (94%, M+—$CO_2$), 231 (M+—$C_3H_4NO$), 202, 44 (100%, $CO_2$). NMR ($CF_3COOH$)=δ1.45 and 1.7 broad (4H in the cyclopropyl radical), 3.9 and 4.0 broad (5H, N—CH in the cyclopropyl radical, N—$CH_2CH_2$—N), 4.6 broad (2H, CO—$CH_2$—N), 7.85 d (1H, on C-8), 8.28 d (1H, on C-5), 9.3 s (1H, on C-2).

After dissolution of the acid in an equivalent amount of 5% strength sodium hydroxide solution and evaporation of the resulting solution, the corresponding sodium salt is obtained. It decomposes above 300° C.

When the corresponding reaction with 7-chloro-1-cyclopropyl-6-fluoro-1,4-dihydro-4-oxo-3-quinolinecarboxylic acid is carried out at 120° C. for 16 hours, then a 12% yield of 1-cyclopropyl-6-fluoro-1,4-dihydro-4-oxo-7-(3-oxo-1-piperazinyl)-3-quinolinecarboxylic acid is obtained.

EXAMPLE 2

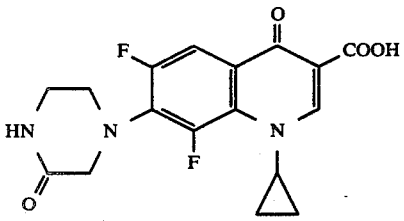

The compound from Example A is reacted with 2-piperazinone in analogy to Example 1, and 1-cyclopropyl-6,8-difluoro-1,4-dihydro-4-oxo-7-(3-oxo-1-piperazinyl)-3quinolinecarboxylic acid of melting point 322°–324° C. (with decomposition) is isolated in 58% yield.

| Example for a tablet according to the invention | |
|---|---|
| Each tablet contains: | |
| Compound of the example | 291.5 mg |
| Mycrocrystalline cellulose | 27.5 mg |
| Corn starch | 36.0 mg |
| Poly(1-vinyl-2-pyrrolidone) insoluble | 15.0 mg |
| Highly disperse silica | 2.5 mg |
| Magnesium stearate | 2.5 mg |
| | 375.0 mg |

| The lacquer coating contains: | |
|---|---|
| Poly(O—hydroxypropyl-O—methyl)cellulose 15 cp (hydroxypropylmethylcellulose USP) | 3.9 mg |
| Macrogol 4000 rec. INN (polyethylene glycols DAB) | 1.3 mg |
| Titanium (IV) oxide (titanium dioxide BP) | 1.3 mg |
| | 6.5 mg |

The compounds according to the invention have low toxicity and exhibit a broad antibacterial spectrum toward Gram-positive and Gram-negative organisms, in particular toward enterobacteriaceae; especially including those which are resistant to various antibiotics, such as, for example, penicillins, cephalosporins, aminoglycosides, sulphonamides and tetracyclines.

These valuable properties make it possible to use them as chemotherapeutic active compounds in medicine and as substances to preserve inorganic and organic materials, especially organic materials of all types, for example polymers, lubricants, dyes, fibers, leather, paper and wood, foodstuffs and water.

The compounds according to the invention are active against a very broad spectrum of microorganisms. Using them, it is possible to combat Gram-negative and Gram-positive bacteria and bacteroid microorganisms, and to prevent, ameliorate and/or heal diseases caused by these pathogens.

The compounds according to the invention are particularly active against bacteria and bacteroid microorganisms. Thus, they are particularly well suited for the prophylaxis and chemotherapy of local and systemic infections caused by these pathogens in human and veterinary medicine.

For example, it is possible to treat and/or prevent local and/or systemic diseases which are caused by the following pathogens or by mixtures of the following pathogens: micrococcaceae, such as staphylococci, for example *Staphylococcus aureus* and *Staph. Epidermidis*, (Staph.=Staphylocoocus); lactobacteriaceae, such as streptoocci for example *Streptococcus pyogenes*, α- and β-haemolytic streptococci, non-γ-haemolytic streptococci, enterococci and *Diplococcus pneumoniae* (pneumococci) (Str.=Streptococcus); enterobacteriaceae, such as Escherichiae bacteria of the coli group: Escherichia bacteria, for example *Escherichia coli*, enterobacteria bacteria, for example *E. aerogenes* and *E. cloacae* (E.=Enterobacter), klebsiella bacteria, for example *K. pneumoniae* (K.=Klebsiella), serratia, for example *Serratia marcescens*, proteae bacteria of the proteus group: Proteus, for example *Pr. vulgaris*, *Pr. morganii*, *Pr. rettgeri* and *Pr. mirabilis* (Pr.=Proteus); pseudomonadaceae, such as Pseudomonas bacteria, for example *Ps. aeruginosa* (Ps.=Pseudomonas); bacteroidaceae, such as bacteroides bacteria, for example *Bacteroides fragilis*; mycoplasma, for example *Mycoplasma pneumoniae*, also mycobacteria, for example *Mycobacterium tuberculosis*, *Mycobacterium leprae* and atypical mycobacteria.

The above list of pathogens is purely illustrative and is in no way to be interpreted as restrictive.

The following may be mentioned as examples of illnesses which can be prevented, ameliorated and/or healed by the compounds according to the invention: otitis; pharyngitis; pneumonia; peritonitis; pyelonephritis; cystitis; endocarditis; systemic infections; bronohitis; arthritis; local infections and septic illnesses.

The present invention includes pharmaceutical preparations which, in addition to non-toxic, inert pharmaceutically suitable vehicles, contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, pills, suppositories and ampules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary vehicles such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol and glycerol monostearate, (h) adsorbents, for example kaolin and bentonite and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acid) or mixtures of these substances.

Ointments, pastes, creams and gels can contain the customary vehicles in addition to the active compound or compounds, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain the customary vehicles in addition to the active compound or compounds, for example lactose, talc, silica, aluminum hydroxide, calcium silicate and polyamide powders, or mixtures of these substances. Sprays can additionally contain the customary propellants, for example chlorofluorohydrocarbons.

Solutions and emulsions can contain the customary vehicles in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example by mixing the active compound or compounds with the vehicle or vehicles.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds in amounts of about 0.5 to about 500, preferably 5 to 100, mg/kg of body weight every 24 hours, optionally in the form of several individual administrations, in order to achieve the desired results. An individual administration contains the active compound or compounds according to the invention preferably in amounts of about 1 to about 250, in particular 3 to 60, mg/kg of body weight. However, it can be necessary to deviate from the dosages mentioned and, in particular, to do so as a function of the nature and body weight of the subject to be treated, the nature and severity of the illness, the nature of the preparation and of the administration of the medicine, and the time or interval over which the administration takes place.

Thus, it can suffice in some cases to manage with less than the abovementioned amount of active compound, whilst in other cases the abovementioned amount of active compound must be exceeded. The particular required optimum dosage and the type of administration of the active compounds can easily be decided by anyone skilled in the art, on the basis of his expert knowledge.

The new compounds can be administered in the customary concentrations and preparations together with the feed or with feed preparations or with the drinking water. By this means, it is possible to prevent, ameliorate and/or heal an infection by Gram-negative or Gram-positive bacteria, and by this means to achieve a promotion of growth and an improvement in the utilization of the feed.

It has already been disclosed, in J. Med. Chem. 23, 1358 (1980), that 1-ethyl-6-fluoro-1,4-dihydro-4-oxo-7-

(1-piperazinyl)-3-quinolinecarboxylic acid (norfloxacin) has antibacterial properties. However, the compounds according to the invention are superior to norfloxacin.

Tables 1 and 2 below show examples of the MIC values of the compound of Example 1 compared with norfloxacin.

|  | MIC (mcg/ml) | | |
| --- | --- | --- | --- |
|  | *Staph.aur.* FK 422 | Staph. 1756 | Staph. 133 |
| Compound of Example 1 | 0.5 | 0.25 | 0.5 |
| Norfloxacin | 2 | 2 | 1 |

TABLE 2

| Microtitre assay/urine (80% pooled human urine, 20% isosensitest medium) | | |
| --- | --- | --- |
|  | MIC mcg/ml urine | |
| Strain | pH 7.1 | pH 7.1 |
| *E. coli* C14 | | |
| Norfloxacin | 4 | 0.5 |
| Compound of Example 1 | 0.25 | 0.25 |
| Staph. 25151 | | |
| Norfloxacin | 4 | 4 |
| Compound of Example 1 | 0.25 | 0.5 |

It will be understood that the specification and exampes are illustrative but not limitative of the present invention and that other embodiments within the spirit and scope of the invention will suggest themselves to those skilled in the art.

We claim:

1. A 1-cyclopropyl-6-fluoro-1,4-dihydro-4-oxo-7-(3-oxo-1-piperazinyl)-3-quinolinecarboxylic acid of the formula

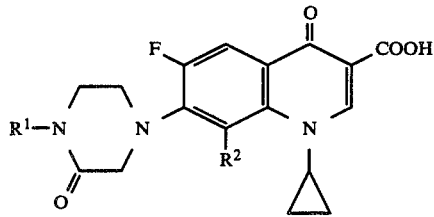

in which
R¹ is hydrogen, methyl or ethyl, and
R² is hydrogen or fluorine, or a pharmaceutically tolerable hydrate or salt thereof.

2. A compound according to claim 1, wherein such compound is 1-cyclopropyl-6-fluoro-1,4-dihydro-4-oxo-7-(3-oxo-1-piperazinyl)-4-quinolinecarboxylic acid or a pharmaceutically tolerable hydrate or salt thereof.

3. A compound according to claim 1, wherein such compound is 1-cyclopropyl-6,8-difluoro-1,4-dihydro-4-oxo-7-(3-oxo-1-piperazinyl)-3-quinolinecarboxylic acid or a pharmaceutically tolerable hydrate or salt thereof.

4. An antibacterial composition comprising an antibacterially effective amount of a compound, hydrate or salt according to claim 1 in admixture with a diluent.

5. A unit dose of a composition according to claim 4 in the form of a tablet, capsule or ampule.

6. A composition according to claim 4, wherein such compound is 1-cyclopropyl-6-fluoro-1,4-dihydro-4-oxo-7-(3-oxo-1-piperazinyl)-4-quinolinecarboxylic acid or a pharmaceutically tolerable hydrate or salt thereof.

7. A composition according to claim 4, wherein such compound is 1-cyclopropyl-6,8-difluoro-1,4-dihydro-4-oxo-7-(3-oxo-1-piperazinyl)-3-quinolinecarboxylic acid or a pharmaceutically tolerable hydrate or salt thereof.

8. A method of combating bacteria which comprises applying to such bacteria or to a bacterial host or habitat an antibacterially effective amount of a compound, hydrate or salt according to claim 1.

9. The method according to claim 8, wherein such compound is 1-cyclopropyl-6-fluoro-1,4-dihydro-4-oxo-7-(3-oxo-1-piperazinyl)-4-quinolinecarboxylic acid or a pharmaceutically tolerable hydrate or salt thereof.

10. The method according to claim 8, wherein such compound is 1-cyclopropyl-6,8-difluoro-1,4-dihydro-4-oxo-7-(3-oxo-1-piperazinyl)-3-quinolinecarboxylic acid or a pharmaceutically tolerable hydrate or salt thereof.

* * * * *

UNITED STATES PATENT AND TRADEMARK OFFICE
CERTIFICATE OF CORRECTION

PATENT NO. : 4,588,726

DATED : May 13, 1986

INVENTOR(S) : Uwe Petersen, et al.

It is certified that error appears in the above-identified patent and that said Letters Patent is hereby corrected as shown below:

| | |
|---|---|
| Col. 4, line 67 | Correct spelling of --quinoline-carboxylic-- |
| Col. 7, line 39 | After "3" insert -- - -- |
| Col. 7, line 46 | Correct spelling of --Microcrystalline-- |
| Col. 8, lines 32, 33 | Delete "enterobacteria" and substitute --enterobacter-- |
| Col. 8, line 52 | Correct spelling of --bronchitis-- |
| Col. 11, line 10 | Insert --Table 1 : Agar dilution test/isosensitest medium-- |
| Col. 11, line 27 | Delete "pH 7.1" first instance and substitute --pH 5.7-- |
| Col. 11, lines 38, 39 | Correct spelling of --examples-- |

Signed and Sealed this

Ninth Day of September 1986

[SEAL]

Attest:

DONALD J. QUIGG

Attesting Officer

Commissioner of Patents and Trademarks